(12) United States Patent
Gilligan et al.

(10) Patent No.: US 6,613,077 B2
(45) Date of Patent: Sep. 2, 2003

(54) STENT WITH CONTROLLED EXPANSION

(75) Inventors: Sean Gilligan, Galway (IR); Barry O'Brien, Galway (IR)

(73) Assignee: SciMed Life Systems, Inc., Maple Grove, MN (US)

(*) Notice: Subject to any disclaimer, the term of this patent is extended or adjusted under 35 U.S.C. 154(b) by 125 days.

(21) Appl. No.: 09/818,338

(22) Filed: Mar. 27, 2001

(65) Prior Publication Data

US 2002/0143381 A1 Oct. 3, 2002

(51) Int. Cl.[7] .................................................. A61F 2/06
(52) U.S. Cl. ..................................... 623/1.12; 623/1.38
(58) Field of Search ....................... 623/1.15, 1.18–1.22, 623/1.2, 1.42, 1.31, 1.3, 1.12, 1.38

(56) References Cited

U.S. PATENT DOCUMENTS

| | | |
|---|---|---|
| 5,201,757 A | 4/1993 | Heyn et al. |
| 5,342,348 A | 8/1994 | Kaplan ..................... 604/891.1 |
| 5,383,928 A | 1/1995 | Scott et al. ................. 623/1.15 |
| 5,476,506 A | 12/1995 | Lunn |
| 5,545,209 A | 8/1996 | Roberts et al. |
| 5,549,662 A | 8/1996 | Fordenbacher |
| 5,575,816 A | 11/1996 | Rudnick et al. |
| 5,591,199 A | 1/1997 | Porter et al. |
| 5,607,463 A | 3/1997 | Schwartz |
| 5,618,300 A | 4/1997 | Marin et al. |
| 5,843,158 A | 12/1998 | Lenker et al. |
| 5,876,432 A | 3/1999 | Lau et al. |
| 5,899,935 A | 5/1999 | Ding |
| 5,957,975 A | 9/1999 | Lafont et al. .............. 623/1.38 |
| 6,001,125 A | 12/1999 | Golds et al. |
| 6,245,100 B1 * | 6/2001 | Davila et al. .............. 623/1.13 |
| 6,331,188 B1 | 12/2001 | Lau et al. ................... 623/1.13 |
| 6,334,868 B1 | 1/2002 | Ham ......................... 623/1.13 |
| 6,336,937 B1 * | 1/2002 | Vonesh et al. ............ 623/1.13 |
| 6,340,368 B1 | 1/2002 | Verbeck .................... 623/1.34 |
| 6,350,277 B1 | 2/2002 | Kocur ....................... 623/1.11 |
| 6,391,052 B2 | 5/2002 | Buirge et al. .............. 623/1.47 |
| 6,423,092 B2 | 7/2002 | Datta et al. ................ 623/1.15 |
| 6,451,052 B1 | 9/2002 | Burmeister et al. ........ 623/1.16 |
| 6,530,949 B2 * | 2/2003 | Konya et al. .............. 623/112 |

FOREIGN PATENT DOCUMENTS

| | | |
|---|---|---|
| EP | 0 923 912 A1 | 6/1999 |
| WO | WO 00/41649 | 7/2000 |
| WO | WO 00/66031 | 11/2000 |

OTHER PUBLICATIONS

Middleton et al., "Synthetic Biodegradable Polymers as Medical Devices", Medical Plastics and Biomaterials Magazine, MPB Article Index, Mar. 1998.

* cited by examiner

Primary Examiner—David H. Willse
Assistant Examiner—Suzette J. Jackson
(74) Attorney, Agent, or Firm—Hoffmann & Baron, LLP

(57) ABSTRACT

An intraluminal prosthesis composed of a self-expandable stent and a biodegradable constraining element being capable of biodegrading in vivo over a predetermined period of time to permit radial expansion of the stent. The constraining elements are applied to the stent to produce a compressed configuration. Dissolution of the constraining elements in vivo allows for expansion of the stent to an expanded configuration.

22 Claims, 2 Drawing Sheets

STENT WITH CONTROLLED EXPANSION

FIELD OF THE INVENTION

The present invention relates to an intraluminal prosthesis having controlled expansion. More particularly, the present invention relates to a stent having controlled radial expansion in vivo to prevent trauma to surrounding tissue.

BACKGROUND OF THE INVENTION

Intraluminal prostheses are medical devices commonly known and used in the treatment of diseased tubular organs, for example, to repair, replace or otherwise correct a defect in a tubular organ, such as a diseased blood vessel. One particular type of intraluminal prosthesis used in the repair of diseases in various body vessels is a stent. A stent is a generally longitudinal tubular device which is useful to open and support various lumens in the body. For example, stents may be used in the vascular system, urogenital tract and bile duct, as well as in a variety of other applications in the body.

Stents are generally open-ended structures which are radially expandable between a compressed insertion diameter and an expanded implantation diameter. Stents are often flexible in configuration, which allows them to be inserted through and conform to tortuous pathways in the blood vessel. Such a stent is generally inserted in a radially compressed state and expanded either through a self-expanding mechanism, or through the use of balloon catheters.

Endovascular stents have become well received for the treatment of stenosis, strictures, and aneurysms in various blood vessels. These devices are implanted within the vessel to open and/or reinforce collapsing or partially occluded sections of the vessel. Such implantation typically involves delivery by way of a catheter advanced through the vascular system to the area of implantation, at which point the stent is released from the catheter and expanded within the blood vessel. It is well known in the art to use a self expanding stent by delivering the compressed stent and then removing the binding support allowing the stent to expand its uncompressed, expanded diameter. It is also well known in the art to use a balloon catheter to expand the stent from an interior expansion position.

Radial expansion of such a stent is typically necessary in order to overcome the stricture-causing blockage to a vessel. Conventional deployment of self-expanding stents, however, typically involves expansion over a very short period of time following release of the stent from the catheter. Such expansion over a short time period can cause undue trauma to surrounding tissue, thereby creating damage which can reduce the effectiveness of the stent, resulting in excessive tissue growth and possible restenosis.

In order to overcome such deficiencies, U.S. Pat. No. 5,843,158 to Lenker et al. proposes a controlled expansion endoluminal prosthesis including a tubular frame stent and a graft, and further having a reinforcing element which limits expansion of the stent-graft at a predetermined expanded size. The reinforcing element can be included in either the stent frame or the graft liner. The '158 patent also discloses that the reinforcing element may be frangible or expansible, which can break or deform under a threshold expansive force to allow further expansion of the frame.

U.S. Pat. No. 5,899,935 to Ding similarly provides for an outer reinforcing element that is deployed in a compressed configuration, and provides an outer expansion limit. However, all of these techniques add additional materials to the prosthesis which remain in the body and add to the thickness of the stent or graft liner. Accordingly, it is desirable to design a stent graft with an outer expansive limit, and a slowed or gradual expansion to protect the luminal surfaces from undue trauma while eliminating the additional thickness of permanent outer structures.

SUMMARY OF THE INVENTION

The present invention is directed to an intraluminal prosthesis including a radially self-expandable intraluminal stent and a biodegradable constraining element which prevents radial expansion of a selected portion of said stent to a fully-expanded diameter. The biodegradable constraining element is capable of biodegrading in vivo over a predetermined period of time to permit radial expansion of the constrained portion of the stent to the fully-expanded diameter.

A method of deploying the prosthesis is also disclosed. The method includes placing the stent into the vessel, permitting the unconstrained portion to radially expand upon deployment, and further permitting the constrained portion to gradually expand over time as the constraining elements biodegrade. Such controlled, gradual expansion decreases the potential for trauma or shock to tissue, particularly tissue which is already compromised, which can be caused by sudden or immediate stent expansion common to self-expanding stents. This promotes the stent effectiveness and acceptance by the body.

DETAILED DESCRIPTION OF THE INVENTION

The present invention relates to an improved expandable stent for intraluminal delivery. Currently available self expanding stents expand with substantially equal force across the length of the stent. As relates to the site of repair or injury, the force of expansion is normally not tolerated by the patient at the site of the repair as well as it is tolerated by the surrounding healthier tissue. In fact, rapid or forceful expansion of a stent graft composite prosthesis can aggravate the site of the injury, or cause further damage. Therefore, one aspect of the present invention provides a stent that engages healthy or less diseased tissue surrounding the diseased site upon delivery and which provides for controlled expansion over time to engage proximal diseased or distressed tissue.

The present invention provides an intraluminal prosthesis that is expandable from a radially contracted condition to a radially expanded condition. The stent exhibits controlled expansion which reduces the rate of self-expansion to protect the surrounding tissue against undue trauma. The invention provides two advantages over current stent delivery methods. First, the expansion is not only limited in direction, but also limited over time, e.g. 4 to 10 days. Second, the constraining member, through the same biodegradable process, is removed and does not add to the permanent thickness of the member.

The stent of the present invention is constrained by constraining elements, e.g. thread sutures. For example, biodegradable sutures sold under the tradename Monocryl (Ethicon, Inc., Somerville, N.J.) may be used. These threads are circumferentially wound tightly around the exterior of a stent to provide a compressed configuration.

The stent of the present invention may be further compressed by a delivery system to facilitate delivery and deployment within a body lumen.

Figure 1:
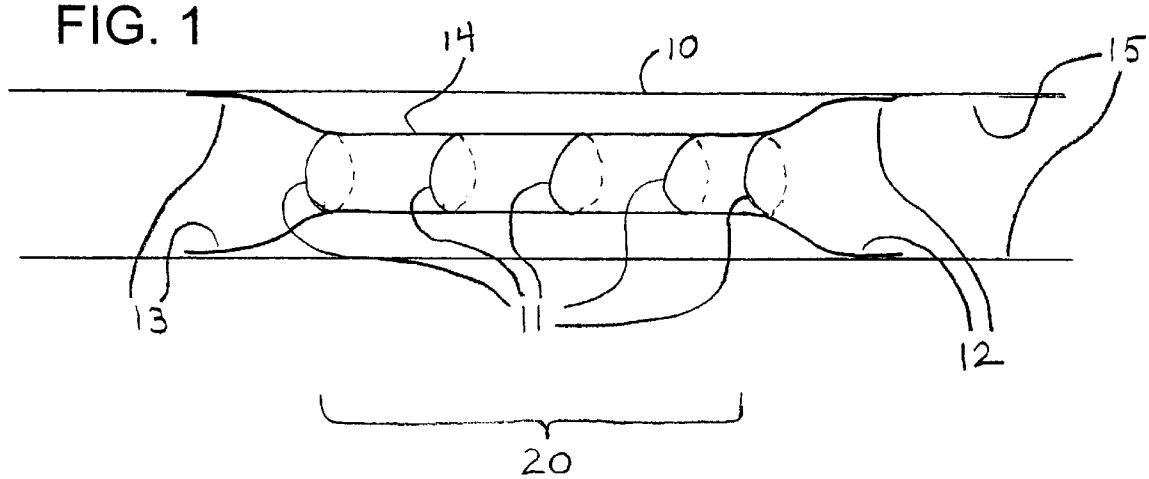
FIG. 1 is a schematic representation of one embodiment of the present invention including a stent implanted in a body vessel, having a central portion circumferentially bound in a radially contracted condition by biodegradable sutures.

FIG. 1 shows a self-expanding stent 14 after deployment within a body lumen such as a blood vessel 10. Stent 14 of FIG. 1 is a schematic representation of a variety of self-expanding stents which may be used in accordance with the present invention. Such stents may take the form of stents 30 and 40 shown respectively in FIGS. 4 and 5. The ends 12 and 13 of the stent 14 have expanded to engage the walls 15 of the vessel 10 after deployment by the delivery system (not shown). In FIG. 1, a medial portion 20 of the stent has been constrained by biodegradable sutures 11, of the type described in further detail hereinbelow. While sutures 11 are shown, other constraining methods are contemplated as hereinafter described. The ends 12 and 13 of the stent 14 have been allowed to engage relatively healthy tissue, while the medial portion 20 is positioned to be spaced away from the diseased tissue. After time, the constraining sutures 11 biodegrade allowing the medial portion 20 of the stent 14 to engage the diseased or damaged tissue. Although the medial portion 20 of the stent 14 is shown as constrained in FIG. 1, various portions of the stent may be similarly temporarily constrained by the biodegradable restraining elements depending on the configuration and intended application.

Figure 2:
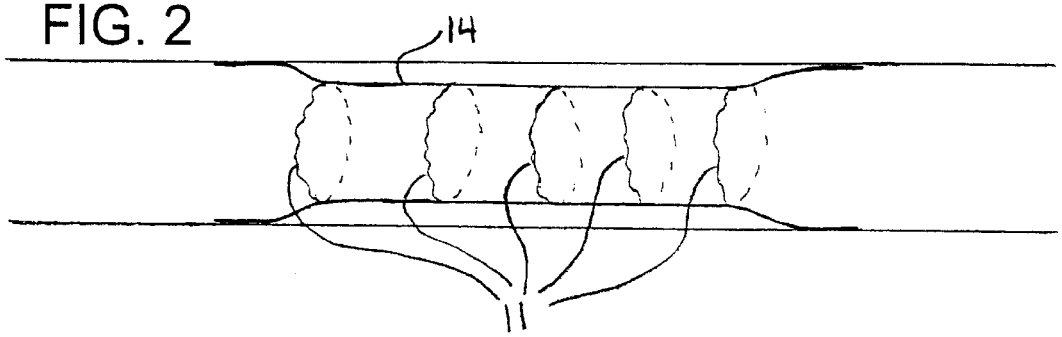
FIG. 2 is a schematic representation of the stent of FIG. 1 where the sutures have partially dissolved allowing gradual expansion of the central portion.

FIG. 2 shows the stent 14 within the vessel as the constraining sutures 11 have begun to biodegrade over time, e.g. three days. As the constraining sutures 11 biodegrade, they begin to yield, allowing the stent 14 to expand.

Figure 3:
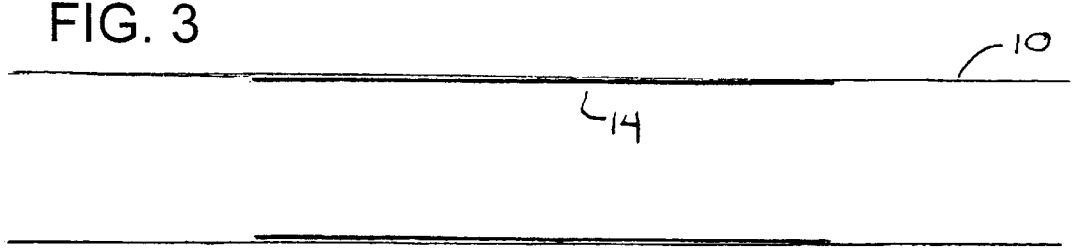
FIG. 3 is a schematic representation of the stent of FIG. 1 where the sutures have fully dissolved and the stent has fully expanded inside the vessel.

FIG. 3 shows the stent 14 in its fully expanded state after the constraining sutures 11 have completely biodegraded, e.g. at approximately 10 days. At this point the stent 14 has engaged the wall 15 of the vessel 10 over the complete length of the stent.

Various parameters can be altered to control expansion. Among those are the configuration and compositional makeup of the constraining elements, the manner in which the constraining elements are attached, as well as the thickness of the constraining elements. Thus, a predetermined degradation rate and controlled expansion rate can be obtained. Typically, dissolution periods of about 4 to about 7 days are desirable, but longer durations, for example, several weeks are also contemplated. The full dissolution of the elements leaves a stent in the expanded configuration as shown in FIG. 3.

Although specifically mentioning thread-like or suture structures, this invention contemplates the use of any biocompatible, biodegradable material and configuration capable of serving as constraining elements. Biodegradable polymers are particularly desirable. Useful polymeric biodegradable materials include polymers, copolymers, block polymers and combinations thereof. Among the known useful polymers or polymer classes which meet the above criteria are: poly(glycolic acid) (PGA), poly(lactic acid) (PLA), polydioxanones, polyoxalates, poly($\alpha$-esters), polyanhydrides, polyacetates, polycaprolactones, poly (orthoesters), and combinations and copolymers thereof. Additional useful polymers include, stereopolymers of L- and D-lactic acid, copolymers of bis(p-carboxyphenoxy) propane acid and sebacic acid, sebacic acid copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Synthetic biocompatible, biodegradable polymers, such as those which break down to substantially non-toxic compounds which are readily absorbed and/or eliminated by the body, are particularly useful.

Other specific polymers useful include those marketed under the Medisorb and Biodel trademarks. The Medisorb® materials are marketed by the DuPont Company of Wilmington, Del. and are generically identified as a "lactide/ glycolide polymer" containing "propanoic acid, 2-hydroxy-polymer with hydroxy-polymer with hydroxyacetic acid." The Biodel® materials represent a family of various polyanhydrides which differ chemically.

The biodegradable constraining element may also include a therapeutic agent that will be released into the body over time as the constraining element is biodegraded. Useful therapeutic agents or drugs include but not limited to, anti-platelets, anti-thrombins, anti-tumor drugs, anti-hyperplasia agents, anti-plaque building agents, cytostatic agents, and anti-proliferative agents, or other drugs for a specific purpose. This may also include agents for gene therapy. The therapeutic agent or drug is preferably selected from the group of therapeutic agents or drugs consisting of urokinase, dextrophenylalanine proline arginine chloromethylketone (PPack), enoxaprin, angiopeptin, acetylsalicylic acid, paclitaxel, 5-fluorouracil, cisplatin, vinblastine, vincristine, sulfasalazine, mesalamine, sodium heparin, low molecular weight heparin, hirudin, prostacyclin and prostacyclin analogues, dextran, glycoprotein IIb/IIIa platelet membrane receptor antibody, recombinant hirudin, thrombin inhibitor, calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, seramin, serotonin blockers, steroids, thioprotease inhibitors, triazolopyrimidine and other PDGF antagonists, alpha-interferon and genetically engineered epithelial cells, and combinations thereof. The foregoing list of therapeutic agents is provided by way of example and is not meant to be limiting, as other therapeutic agents and drugs may be developed which are equally applicable for use with the present invention.

The prosthesis is desirably constructed to be of a tubular configuration, having a lumen therethrough, with opposing end portions and a medial portion. In one aspect of the invention, constraining elements are applied selectively to the medial portion of the stent so as to limit the expansion of the medial portion, while allowing the end portions to be free to engage the lumen or blood vessel wall. One advantage of this construction is that the end portions can be positioned to engage relatively healthy tissue surrounding the site of the stenosis or structural defect, avoiding trauma to the weakened tissue.

Further, the materials of the constraining element can be chosen to provide gradual and controlled expansion of the stent over time. In addition, the construction of the constraining elements and configuration about the stent can be chosen in such a manner as to allow for partial expansion of the stent to an intermediate diameter while allowing further expansion to transpire over time as the constraining elements biodegrade or bioabsorb whereby the stent is allowed to expand to its fully self-expanding diameter. Materials can be chosen to provide constraining elements that degrade relatively quickly to allow for faster expansion to the fully-expanded diameter. Additional materials or thicknesses of materials can then be chosen to provide constraining elements that degrade or bioabsorb over a longer period of time to provide delayed expansion to the fully-expanded diameter. For example, a combination of faster and slower degradable materials may be used. Such a combination may be employed as individual filaments or threads which make up a single suture or yarn, or multiple sutures, each having a different biodegradation rate may be used.

In the operation of devices of the present invention, there is provided a multiple step expansion process or sequence. The first expansion occurs by the unconstrained portions once the stent is deployed. Delivery of the stent is desirably by catheter, the stent being in a compressed diameter along its length to facilitate delivery. In one aspect of the invention, the delivery system includes a catheter and sheath for holding the stent in a compressed diameter along its length. In such an embodiment, the unconstrained portions of the stent are free to self-expand once the sheath is pulled back as the stent is deployed.

Other delivery systems and methods are also contemplated and may be used with the present invention. For example, the stent may be affixed to a balloon catheter using various mechanical means such as creating a releasable bond between the stent and catheter balloon. When the delivery catheter is removed, the ends of the prosthesis will expand fully to engage with the healthy surrounding tissue, while the medial portions of the prosthesis will expand only until the limits of the constraining members are reached. Thereafter, the slower expansion of the medial portion will transpire as the constraining members are bioabsorbed or biodegraded, thereby creating additional, gradual expansion steps.

In another embodiment of the invention, there is provided one or more constraining elements to be helically wrapped around the stent to provide constraining from full expansion. Alternatively, an arrangement of constraining elements may be axially spaced and circumferentially wrapped about the portion of the stent to be radially constrained.

In another aspect of the invention there is provided a stent composed of an undulating series of waves which are helically configured to form a tube. Thereafter a constraining element is provided that is intertwined between the waves of the stent to compress selected portions of the stent.

In another embodiment of the present invention, it is desirable to provide a stent graft combination, the combination prostheses composed of a tubular graft coupled to the interior surface of the stent.

As previously mentioned, the stent of the prosthesis may be chosen from a wide variety of materials and configurations. Examples of useful stents and grafts for the present invention are shown in FIGS. 4 and 5.

Figure 4:
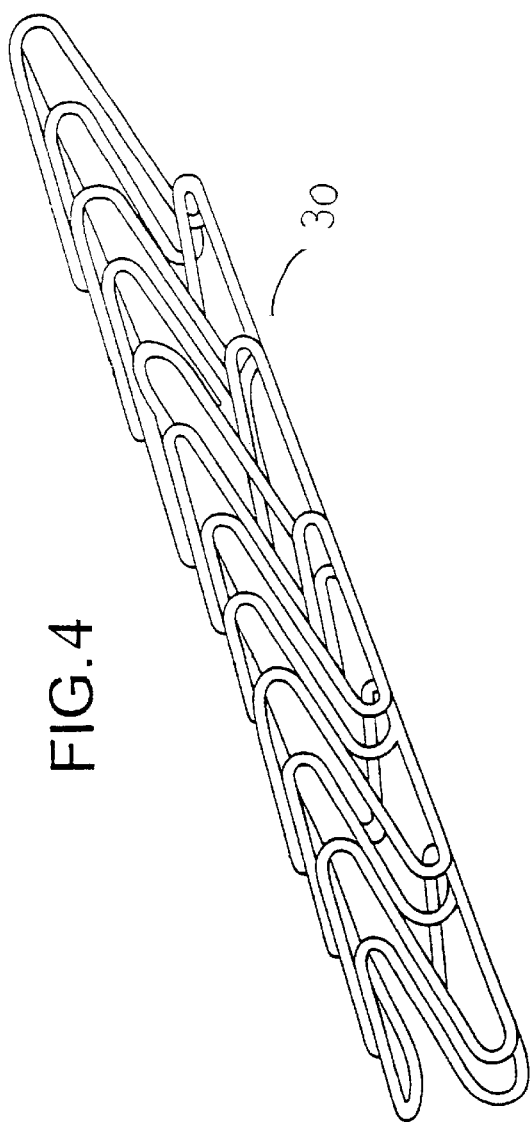
FIG. 4 shows an example of a type of stent that may be employed in the present invention.
Figure 5:
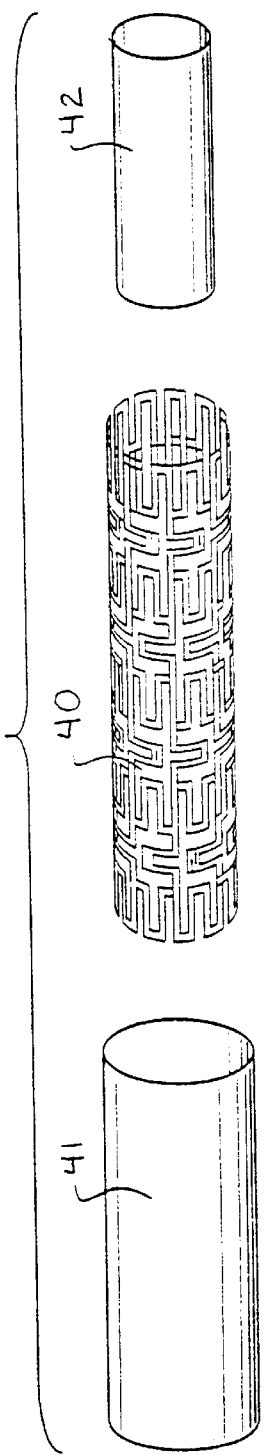
FIG. 5 shows another example of a stent along with a stent covering and a stent liner that may be employed in the present invention.

FIG. 4 shows a nested wire stent. The nested stent 30 is expandable from a radially contracted condition shown in FIG. 4 to an expanded condition. The stent 30 is more fully shown and described in U.S. Pat. No. 5,575,816 to Rudnick et al. which is incorporated herein by reference for all purposes. Other stent types, such as tubular-shaped wire stents and self-expandable spring-based stents are also contemplated. Self-expanding stents include those that have a spring-like action which causes the stent to radially expand, or stents which expand due to the memory properties of the stent material for a particular configuration at a certain temperature.

The stent may be made from a variety of materials including stainless steel, titanium, platinum, gold and other bio-compatible metals. Thermoplastic materials which are inert in the body may also be employed. Shaped memory alloys having superelastic properties generally made from specific ratios of nickel and titanium, commonly known as nitinol, are among the preferred stent materials. Nitinol is one material which has the ability to perform well while both in spring-like mode, as well as in a memory mode based on temperature. Other materials are of course contemplated, such as stainless steel, platinum, gold, titanium and other bio-compatible metals, as well as polymeric stents.

As mentioned above, combined stent-graft devices are also useful in this invention. Composite stent-graft devices employing tubular structures are also known wherein a stent is provided with one or both of a polymeric cover disposed at least partially about the exterior surface of the stent and a polymeric liner disposed about the interior surface of the stent. FIG. 5 shows an example a slotted tubular stent 40 formed of a temperature sensitive memory alloy which changes shape at a designated temperature range. The stent 40 may optionally include a cover 41 and a liner 42. The composite prosthesis shown in FIG. 5 is more fully shown and described in U.S. Pat. No. 6,001,125 to Golds et al. which is incorporated herein by reference for all purposes. These composite devices have the beneficial aspects of a stent, which is used to hold open a blocked or occluded vessel, and also a graft which is used to replace or repair a damaged vessel. Several types of stent-grafts utilize fibrous grafts having porosity conducive to tissue ingrowth and elasticity conducive to expansion and contraction within a fluid environment. Often, fibers of various materials are used, alone or in combination, to form graft structures that accentuate the positive effects of stents on their vascular environment. Use of fibers obviates the need to shape and mold a device into its ultimate working configuration, and many fibers have proven to be biocompatible with vascular tissues.

Vascular grafts may be fabricated from a multitude of materials, such as synthetic textile materials and fluoropolymers (i.e. expanded polytetrafluoroethylene (ePTFE)) and polyolefinic material such as polyethylene and polypropylene. Nylon is often used, but polyester is chosen more frequently because of its good mechanical and chemical properties. Polyester is the most commonly used because it is available in a wide range of linear densities and its low moisture absorption also gives good resistance to fast deterioration. Polyurethane is another polymer especially used for its elasticity. Graft material selection is not limited to those materials listed above, but may include others that are conducive to the biocompatibility, distensibility and microporosity requirements of endovascular applications.

Other stent-graft devices are known in the art. Examples of such stent-graft composite devices which may be used in accordance with the present invention are shown in U.S. Pat. No. 5,476,506 to Lunn; U.S. Pat. No. 5,591,199 to Porter et al.; U.S. Pat. No. 5,591,223 to Lock et al.; and U.S. Pat. No. 5,607,463 to Schwartz et al.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. An intraluminal prosthesis comprising:
   a. an intraluminal stent comprising opposing end portions and a medial portion therebetween, said stent being radially self-expandable between a compressed diameter and a fully-expanded diameter; and
   b. a biodegradable constraining element applied to said stent so as to prevent radial expansion of said medial portion of said stent to said fully-expanded diameter, thereby limiting radial expansion of said medial portion of said stent to a diameter intermediate of said compressed and fully expanded diameters said biodegradable constraining element biodegrading in vivo over a period of time to permit radial expansion of said portion of said stent to said fully-expanded diameter;
   wherein said opposing end portions are not constrained and therefore are permitted to expand to the fully-expanded diameter, contacting a vessel wall upon implantation.

2. An intraluminal prosthesis as in claim 1, wherein said biodegradable constraining element comprises a biodegradable suture helically wrapped about said selected portion of said stent.

3. An intraluminal prosthesis as in claim 1, wherein said biodegradable constraining element comprises a plurality of biodegradable sutures circumferentially wrapped about said selected portion of said stent at axially-spaced positions.

4. An intraluminal prosthesis as in claim 1, wherein said stent comprises an undulating member helically wound along a longitudinal axis, forming a series of waves.

5. An intraluminal prosthesis as in claim 4, wherein said biodegradable constraining element is intertwined between said waves at said selected portion of said stent.

6. An intraluminal prosthesis as in claim 1, wherein said biodegradable constraining element is constructed of a material selected from the group consisting of poly(glycolic acid) (PGA), poly(lactic acid)(PLA), polydioxanones, polyoxalates, poly($\alpha$-esters), polyanhydrides, polyacetates, polycaprolactones, poly(orthoesters), stereopolymers of L- and D-lactic acid, copolymers of bis(p-carboxyphenoxy) propane acid and sebacic acid, sebacic acid copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and combinations and copolymers thereof.

7. An intraluminal prosthesis as in claim 1, wherein said biodegradable constraining element further comprises a therapeutic agent.

8. An intraluminal prosthesis as in claim 1, wherein said stent is constructed of a material selected from the group consisting of stainless steel, titanium, platinum, gold, nickel/titanium alloys, nitinol, bio-compatible metals, and inert thermoplastic materials.

9. An intraluminal prosthesis as in claim 1, further including a tubular graft coaxially coupled to said stent.

10. An intraluminal prosthesis as in claim 9, wherein said tubular graft is coaxially placed on an interior surface of said stent.

11. An intraluminal prosthesis as in claim 9, wherein said tubular graft is coaxially place on an exterior surface of said stent.

12. An intraluminal prosthesis as in claim 1, wherein said stent comprises a series of connected elongate strut portions having openings therebetween.

13. An intraluminal prosthesis as in claim 1, wherein said stent self-expands by a spring-like bias.

14. An intraluminal prosthesis as in claim 1, wherein said stent self-expands by shape memory properties.

15. An intraluminal prosthesis as in claim 1, wherein said stent has superelastic properties.

16. A method of implanting an intraluminal prosthesis within a vessel comprising:
   a. providing, in a compressed first diameter, a radially self-expanding stent having opposed end portions and a medial portion therebetween, said medial portion of said stent being held in said compressed first diameter by a biodegradable constraining element;
   b. delivering said stent within a vessel to an area of implantation;
   c. permitting an unconstrained portion of said stent comprising said opposed end portions to radially expand to a second diameter; and thereby engage a vessel wall; and
   d. permitting in vivo biodegradation of said biodegradable constraining elements to permit said portion of said stent being held in said first compressed diameter to radially expand.

17. A method of making an intraluminal prosthesis comprising the steps of:
   a providing a radially self-expanding tubular stent defining a lumen therein comprising first and second ends and a medial portion therebetween;
   b. placing a biodegradable constraining element on said stent to constrain said medial portion of said stent from diametrically changing to a radially expanded state.

18. An intraluminal prosthesis as in claim 17, wherein said constraining element is wrapped about the length of said stent in a helical fashion.

19. An intraluminal prosthesis as in claim 17, wherein said constraining element is wrapped circumferentially about a portion of said stent.

20. An intraluminal prosthesis as in claim 17, wherein multiple constraining elements are placed along the length of said stent.

21. An intraluminal prosthesis as in claim 17, wherein said constraining element is placed on said stent while said stent is in the partially radially compressed state.

22. An intraluminal prosthesis as in claim 17, wherein said constraining element further comprises a therapeutic agent.

* * * * *

UNITED STATES PATENT AND TRADEMARK OFFICE
CERTIFICATE OF CORRECTION

PATENT NO. : 6,613,077 B2
DATED : September 2, 2003
INVENTOR(S) : Gilligan et al.

It is certified that error appears in the above-identified patent and that said Letters Patent is hereby corrected as shown below:

Column 6,
Line 28, should read -- ..example of a slotted... --.

Signed and Sealed this

Sixteenth Day of December, 2003

JAMES E. ROGAN
*Director of the United States Patent and Trademark Office*